United States Patent
Kanazawa et al.

(10) Patent No.: US 7,537,343 B2
(45) Date of Patent: May 26, 2009

(54) OPTOTYPE PRESENTING APPARATUS

(75) Inventors: Yuichiro Kanazawa, Okazaki (JP); Tatefumi Oda, Nukata-gun (JP)

(73) Assignee: Nidek Co., Ltd., Gamagori (JP)

(*) Notice: Subject to any disclaimer, the term of this patent is extended or adjusted under 35 U.S.C. 154(b) by 29 days.

(21) Appl. No.: 11/826,625

(22) Filed: Jul. 17, 2007

(65) Prior Publication Data

US 2008/0018858 A1    Jan. 24, 2008

(30) Foreign Application Priority Data

Jul. 21, 2006    (JP) .............................. 2006-200121

(51) Int. Cl.
*A61B 3/02*    (2006.01)
(52) U.S. Cl. ..................... 351/239; 351/237
(58) Field of Classification Search ................ 351/200, 351/237, 239, 211
See application file for complete search history.

(56) References Cited

U.S. PATENT DOCUMENTS

| | | | |
|---|---|---|---|
| 5,589,897 A * | 12/1996 | Sinclair et al. .............. | 351/223 |
| 5,877,841 A | 3/1999 | Jeon ........................... | 248/519 |
| 5,880,814 A * | 3/1999 | McKnight et al. ........... | 351/239 |
| 6,425,665 B2 | 7/2002 | Hayashi et al. .............. | 351/239 |
| 7,220,000 B2 * | 5/2007 | Alster et al. ................. | 351/224 |
| 2001/0043309 A1 | 11/2001 | Hayashi et al. .............. | 351/243 |
| 2004/0105073 A1 | 6/2004 | Maddalena et al. .......... | 351/205 |

FOREIGN PATENT DOCUMENTS

| | | |
|---|---|---|
| EP | 1 138 251 A1 | 10/2001 |
| JP | A 5-337083 | 12/1993 |
| JP | A 6-254050 | 9/1994 |
| JP | A 2006-42978 | 2/2006 |
| WO | WO 02/00105 A1 | 1/2002 |
| WO | WO 03/070089 A1 | 8/2003 |

* cited by examiner

*Primary Examiner*—Mohammed Hasan
(74) *Attorney, Agent, or Firm*—Oliff & Berridge, PLC

(57) ABSTRACT

An optotype presenting apparatus for testing a visual function of an eye of an examinee comprises: a display unit including a display which displays various optotypes by controlling a number of pixels and a memory in which the optotypes to be displayed on the display are stored; an operation unit for inputting a selection signal to select an optotype to be displayed on the display; and a display control unit for switching an optotype to the selected optotype in such a manner as to cause the optotype displayed before switching to disappear in response to the selection signal and then display the selected optotype after 0.05 second to 1.0 second from the disappearance of the optotype displayed before switching.

10 Claims, 4 Drawing Sheets

FIG. 3A  FIG. 3B  FIG. 3C
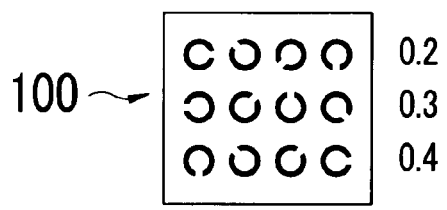
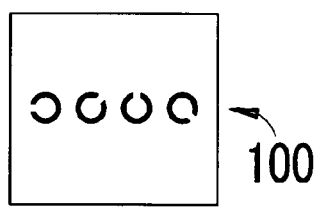
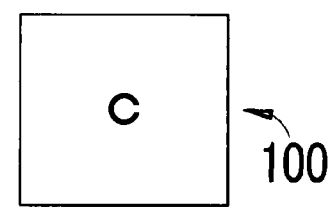
FIG. 3D  FIG. 3E
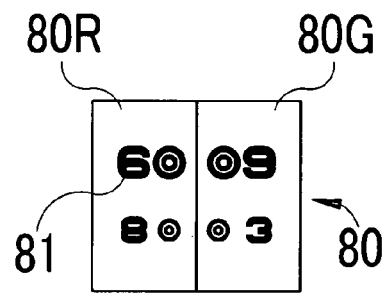
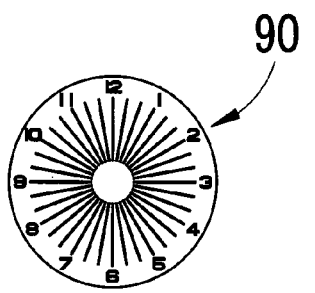
FIG. 3F  FIG. 3G
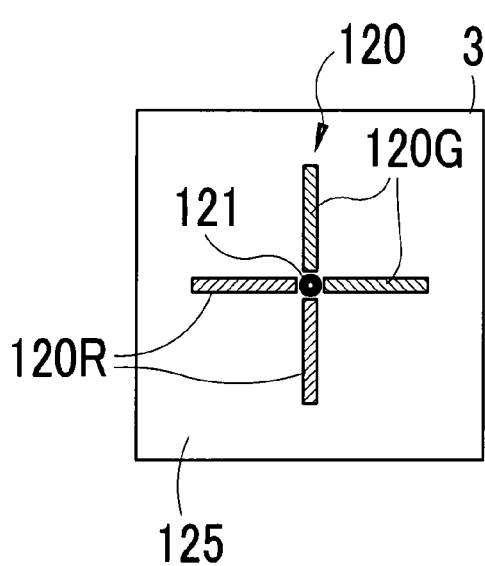
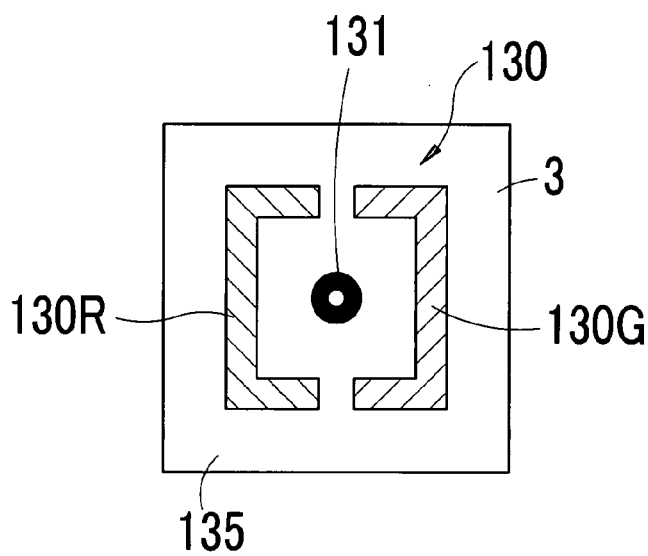

101

102

OPTOTYPE PRESENTING APPARATUS

BACKGROUND OF THE INVENTION

1. Field of the Invention

The present invention relates to an optotype presenting apparatus arranged to present test optotypes for testing a visual function of an examinee's eye.

2. Description of Related Art

An optotype presenting apparatus arranged to display vision test optotypes (charts) on a display such as a liquid crystal display and present the optotypes to examinee's eyes has ever been known (for example, see Jpn. unexamined patent publication No. 2006-42978). The optotype presenting apparatus of this type is located in use at a 5-m distance or others for a far vision test.

Meanwhile, the apparatus configured to display the optotypes on the display can present various kinds of optotypes and quickly switch to another on the display.

The case where the vision test optotypes for almost equal visual acuity are selectively displayed in almost the same position of the display is mentioned below. In this case, when an optotype or chart is quickly switched to another, an examiner and an examinee may not instantly perceive that the optotype or chart has been switched to another. Thus, a test could not be conducted smoothly. In the case where Landolt ring optotypes or tumbling E optotypes are selectively displayed by changing only their orientations, particularly, it is likely to be more difficult for the examiner and the examinee to perceive the optotype or chart having been switched as the optotypes are smaller in size.

BRIEF SUMMARY OF THE INVENTION

The present invention has an object to provide an optotype presenting apparatus arranged to allow an examiner and an examinee to readily perceive switching to another optotype or chart for smoothly conducting tests.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided an optotype presenting apparatus for testing a visual function of an eye of an examinee, the apparatus comprising: a display unit including a display which displays various optotypes by controlling a number of pixels and a memory in which the optotypes to be displayed on the display are stored; an operation unit for inputting a selection signal to select an optotype to be displayed on the display; and a display control unit for switching an optotype to the selected optotype in such a manner as to cause the optotype displayed before switching to disappear in response to the selection signal and then display the selected optotype after 0.05 second to 1.0 second from the disappearance of the optotype displayed before switching.

According to another aspect, the invention provides an optotype presenting apparatus for testing a visual function of an eye of an examinee, the apparatus comprising: a display unit including a display which displays various optotypes by controlling a number of pixels and a memory in which the optotypes to be displayed on the display are stored; an operation unit for inputting a selection signal to select an optotype to be displayed on the display; and a display control unit for switching an optotype to the selected optotype in such a manner as to cause the optotype displayed before switching to disappear in response to the selection signal and then display the selected optotype after 0.05 second to 1.0 second from the disappearance of the optotype displayed before switching.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings,

FIGS. 3A to 3G are explanatory views to show optotypes to be displayed on a display.

DETAILED DESCRIPTION OF THE PREFERRED EMBODIMENTS

Figure 1:
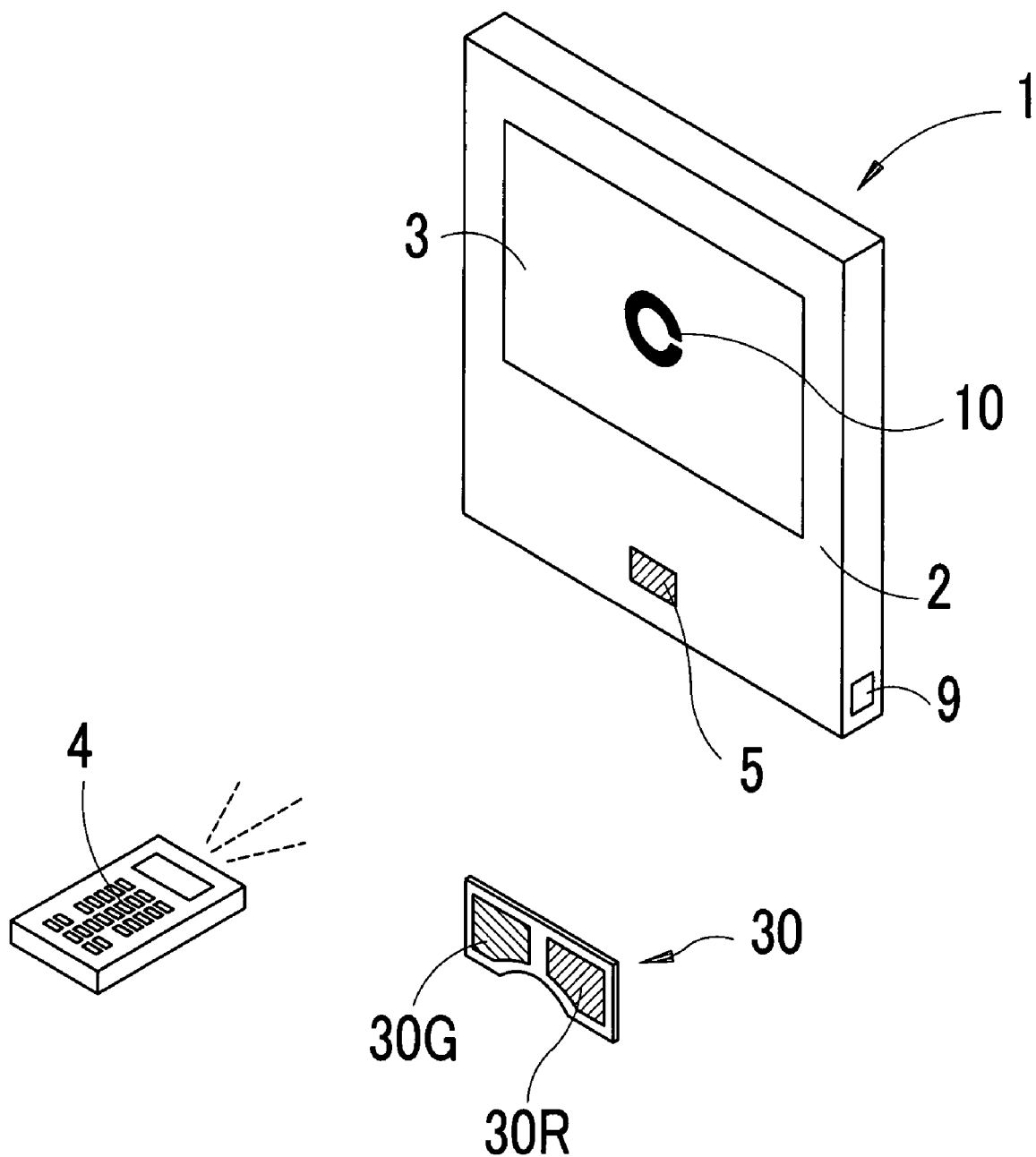
FIG. 1 is an external view of an optotype presenting apparatus of a preferred embodiment according to the present invention.

A detailed description of a preferred embodiment of the present invention will now be given referring to the accompanying drawings. FIG. 1 is an external view of an optotype presenting apparatus of the present embodiment.

At a front surface of a housing 2 of an optotype presenting apparatus 1, a color liquid crystal display (LCD) 3 is provided to present optotypes (charts). This display 3 used in the present embodiment has a 19-inch size to display a predetermined size of a test optotype 10 such as vision test optotypes for visual acuity of at least 0.1 to 2.0 (or vision test optotypes of sizes corresponding to the visual acuity), red-green test optotypes, and binocular vision test optotypes even where the apparatus is placed at a distance for a far vision test, e.g., 5 m. Further, the housing 2 is designed to have a thickness of as small as about 5 cm for allowing wall-mounted use.

At a lower part of the front surface of the housing 2, a receiver 5 which receives a communication signal of infrared light from a remote controller 4 is provided. The optotype 10 to be displayed is selected by operation of the remote controller 4. In the present embodiment, optotypes for visual acuity of 0.03 to 2.0 can be displayed. When a single optotype is to be presented, the optotype 10 is displayed in almost the center of the display 3. In the case where the optotype presenting apparatus 1 is used in combination with a subjective refractive power test device (a horopter) arranged to selectively place optical elements (see Jpn. unexamined patent publication No. 5(1993)-337083, for example), it is preferable to align the optical center of each optical element and the center of each optotype with an optical axis of an examinee's eye. This is to prevent deterioration in accuracy of an astigmatism test using the optical elements including a cylindrical lens, which could be caused by deviation of a visual line of the examinee's eye from the optical center of the presented optical element.

Red-green spectacles 30 have a red filter 30R for a right eye and a green filter 30G for a left eye. Using the red-green spectacles 30, a binocular vision test on the examinee is carried out.

Figure 2:
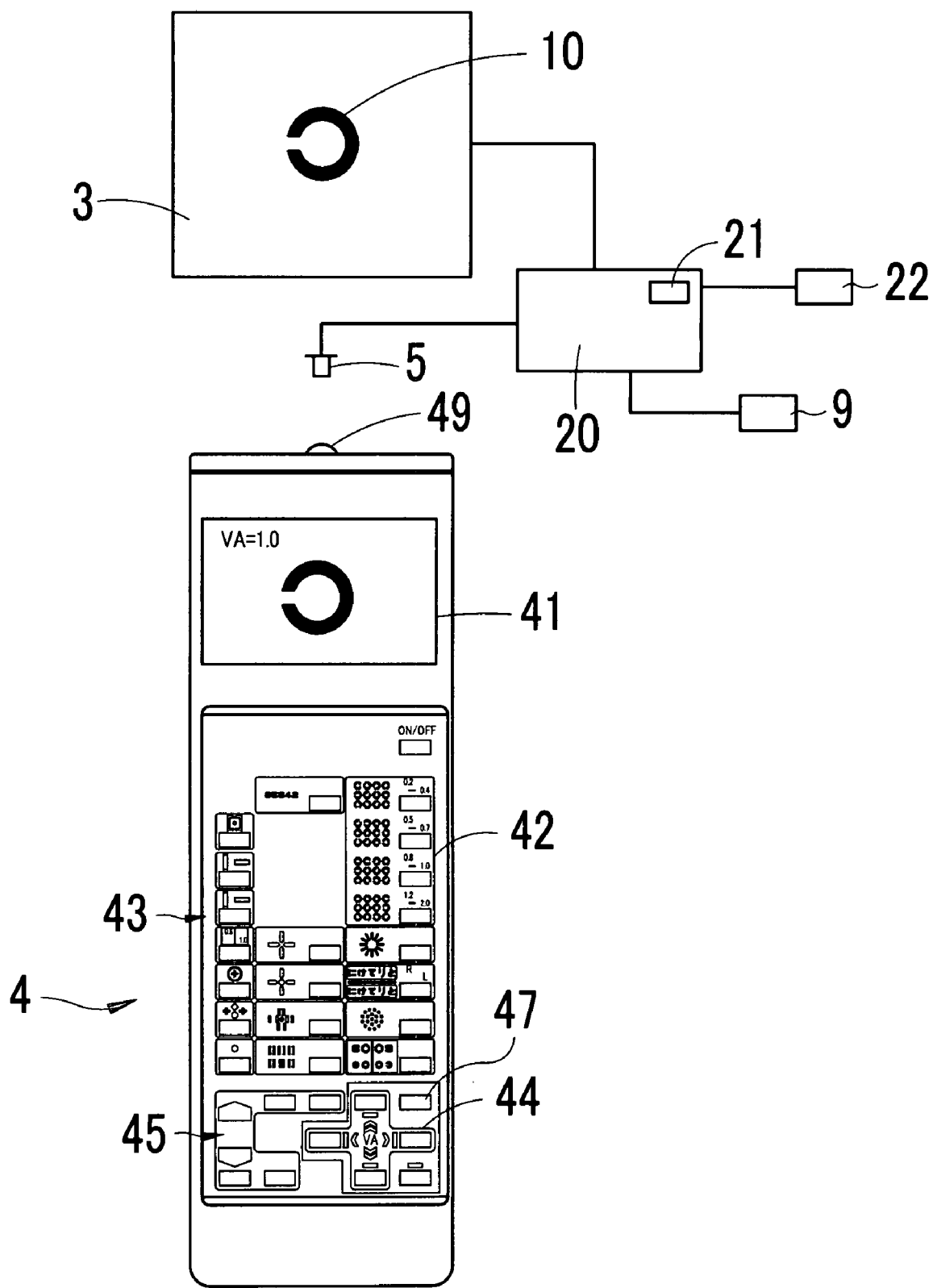
FIG. 2 is a schematic control block diagram.

FIG. 2 is a schematic control block diagram of the optotype presenting apparatus 1 of the present embodiment. The display 3, the receiver 5, and a buzzer 9 for informing that the receiver 5 has received a signal from the remote controller 4 are connected to a control unit 20. The control unit 20 internally contains a memory 21 which stores various figures or patterns of optotypes or charts and a decoder circuit which decodes command signals from the remote controller 4.

The remote controller 4 includes a plurality of buttons to be used for operating an apparatus main unit, and a liquid crystal display 41 which displays conditions selected with the buttons. At the press of a button(s) of a vision optotype selector switch section 42 corresponding to visual acuity, an optotype corresponding to the visual acuity is displayed on the display 3. At this time, the same optotype is also displayed on the display 41 as well as the visual acuity. A test optotype selector switch section 43 is operated to display optotypes for various vision tests such as a red-green test, a cross-cylinder test, and a binocular vision test. An orientation selecting button 44 is pressed to change the orientation of the currently displayed optotype. A visual acuity up/down button 45 is pressed to increase or decrease the visual acuity. An optotype selecting button 47 is pressed to change a display pattern of the vision test optotypes on the display 3 from optotypes arranged in a horizontal line or a single letter optotype. A transmitter 49 transmits a command signal from the remote controller 4.

FIGS. 3A to 3G are explanatory views to show the optotype 10 to be displayed on the display 3. FIGS. 3A to 3C show Landolt rings in a vision test chart 100. When any button of the switch section 42 is pressed, the optotypes corresponding to the selected visual acuity are displayed in three horizontal lines as shown in FIG. 3A. In each line, four optotypes are arranged. In this example, the optotypes in a top line correspond to visual acuity 0.2, the optotypes in a middle line correspond to visual acuity 0.3, and the optotypes in a bottom line correspond to visual acuity 0.4. The optotypes in FIG. 3A are illustrated in the same size for convenience of explanation: The optotypes arranged in each line appear with gaps (slits) oriented in different directions. At the press of other buttons of the switch section 42, the optotypes are switched to optotypes for visual acuity of 0.5, 0.6, 0.7 arranged in three lines, a chart with optotypes for visual acuity of 0.8, 0.9, 1.0 arranged in three lines, or a chart with optotypes for visual acuity of 1.2, 1.5, 2.0.

When the button 47 is pressed while the three-line optotypes are appearing as shown in FIG. 3A, the screen image of the display 3 is switched to optotypes arranged in a single line as shown in FIG. 3B. When the button 47 is pressed again, it is switched to a single letter optotype arranged in the center of the display as shown in FIG. 3C. The direction of a gap of this optotype to be displayed is determined randomly by the control unit 20.

As the vision test optotypes (charts), Landolt rings are explained as an example. Further, the tumbling E optotypes for making an examinee indicate orientations of the optotypes are also stored in the memory 21. Alternatively, as vision test optotypes (charts) used for making an examinee identify letters, various kinds of test optotypes such as Hiragana (Japanese characteristics) optotypes, alphabet optotypes, and number optotypes are stored in the memory 21. Those optotypes can be selected with a selecting unit 22 connected to the control unit 20 according to countries or regions in which the apparatus is used.

FIG. 3D shows an example of a red-green chart 80 used to determine overcorrection in a refractive power test. This chart 80 has a left-half red background 80R and a right-half green background 80G. If an examinee can see a graphic optotype 81 on the green background 80G sharper than a graphic optotype 81 on the red background 80R, correcting power is considered as overcorrection. In this case, the examiner should adjust spherical power appropriate for the examinee's eye so that the optotypes 81 on the backgrounds 80G and 80R appear equal or the graphic optotype 81 on the red background 80R appears clearer. FIG. 3E shows an example of a radial line chart (a clock dial chart) 90 for astigmatism test.

FIG. 3F shows an example of a heterophoria test chart 120 with a fusion optotype for binocular vision test. In the binocular vision test using the present apparatus, the red-green spectacles 30 is used. In FIG. 3F, a background screen 125 of the display 3 appears in white. Presented figures 120G (a first figure) to be presented to only a right eye through the red filter 30R are displayed in green. On the other hand, presented figure 120R (a second figure) to be presented to only a left eye through the green filter 30G are displayed in red. A fusion optotype 121 to be presented to both eyes at the same time is displayed in black. The heterophoria test charts may include Cross-ring charts, Worth four-point charts, and Cyclophoria charts, which can selectively be displayed.

FIG. 3G shows an example of an aniseiconia test chart 130 for binocular vision test. A background screen 135 is displayed in white. A presented figure 130G to be presented to only a right eye through the red filter 30R is displayed in green. A presented figure 130R to be presented to only a left eye through the green filter 30G is displayed in red. A fusion optotype 131 to be presented to both eyes at the same time is displayed in black. The charts for binocular vision test may include stereo vision test charts not illustrated here.

The display 3 has a screen size capable of displaying the visual acuity test chart with the optotypes arranged in horizontal three lines or in a horizontal line as above, the red-green chart, the binocular vision test chart, and others even where the apparatus is placed at a distance for far vision test, e.g., 5 m from the examinee's eyes.

Characteristic operations of the invention are explained below. The examiner operates various buttons on the remote controller 4 to switch the test optotypes (charts) to conduct vision tests. Displaying of the test optotypes (charts) on the display 3 is controlled by the control unit 20 in response to an optotype switching (selection) signal output from the remote controller 4.

Figure 4A:
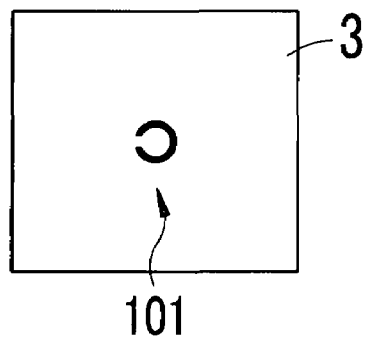
FIGS. 4A to 4C are explanatory views to show switching of a single letter optotype for visual acuity test to another optotype.
Figure 4B:
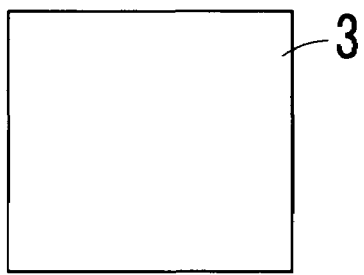
Figure 4C:
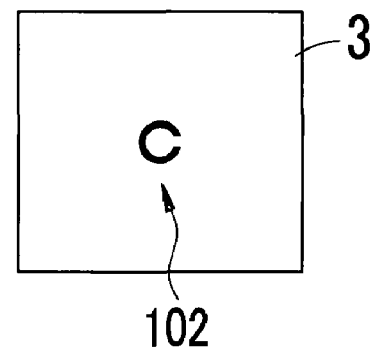

An example of switching single letter optotypes in the vision test chart 100 is explained referring to FIGS. 4A to 4C. The single letter optotype of the vision test chart is displayed in such a manner that a button of the switch section 42 corresponding to desired visual acuity is pressed, displaying optotypes in three lines, and then the button 47 is pressed. This single letter optotype appears in the center of the display 3. FIG. 4A shows a case where a Landolt ring 101 with a leftward gap is displayed. When any button 44 is pressed, the Landolt ring is switched to another Landolt ring with a different-side gap while having the same center position and visual acuity. FIG. 4C shows a Landolt ring 102 with a rightward gap. The optotype 101 in FIG. 4A and the optotype 102 in FIG. 4C are equal in visual acuity and different only in gap position.

Here, the switching of the screen image of the display 3 is usually performed immediately by the control unit 20. If switching from the optotype 101 to the optotype 102 is also conducted immediately, the examinee cannot identify the switching to the optotype 102 even when he/she looks at the display 3 if his/her visual acuity is not sufficiently high as compared with visual acuity of the displayed optotype (or if he/she can barely read the optotype). The same applies to the examiner. If the examiner could not certainly identify the switching to another optotype, he/she cannot determine reliably whether or not a response of the examinee is correct. Thus, the test could not be conducted smoothly. Further, when a Landolt ring is switched to another with a gap oriented in a different direction, some examinees can take notice of the position of the gap because a black portion of the previous Landolt ring immediately switches to a white portion. In this case, test accuracy will deteriorate.

Switching of optotypes or charts may also be informed by a sound generated from the buzzer 9. However, if an examinee is difficult in hearing or if test environment is noisy, the sound may be insufficient to inform the switching.

If an optotype switching signal transmitted from the transmitter 49 of the remote controller 4 is not received by the receiver 5 due to any malfunction or fault, the optotype on the display 3 cannot be switched to another by the control unit 20. On the other hand, the screen image of the display 41 of the remote controller 4 can be switched by the optotype switching signal. In this case, when the examiner does not perceive the switching of the optotype on the display 3, he/she may give erroneous decision by looking the optotype displayed on the display 41.

In the apparatus of the invention, for switching the optotype 101 in FIG. 4A to the optotype 102 in FIG. 4C, the control unit 20 controls the screen image of the display 3 to cause the test optotype to disappear once as shown in FIG. 4B for a duration of time T needed for the examiner/examinee to readily identify the switching without immediately switching the optotype 101 to the optotype 102 in a conventional manner. The time T for which the optotype disappears is set to 0.2 second in the present embodiment. By this disappearance time T, both the examinee and the examiner can readily perceive the switching of optotype even in switching of small-sized optotype hard to perceive.

The disappearance time T is not limited to 0.2 second and may variously be set to appropriate values. The disappearance time T has to be long enough to make a person who looks at the display 3 reliably identify that a disappearance state has passed. A human eye can continuously perceive changes at a speed of 1/30 second. Accordingly, the disappearance time T is preferably determined to be longer such speed, i.e., to be 0.05 second or more. On the contrary, if the disappearance time T is too long, on the other hand, a person who looks at the display 3 may feel that the time until the optotype is switched to another is lengthy. Considering this problem, the disappearance time T is preferably 0.05 second to 1.0 second and, more preferably, 0.1 second to 0.5 second.

The above explanation is made on the case of switching of the visual acuity test optotypes equal in visual acuity (equal in size). In the present embodiment, furthermore, when a currently displayed test optotype is to be switched to a test optotype of larger or smaller visual acuity set with the button 45, the next test optotype is displayed after the time T from disappearance of the current optotype. In displaying the optotypes arranged in several horizontal lines as in FIG. 3A or the optotypes arranged in a horizontal single line as in FIG. 3B, similarly, the next test optotypes are displayed after the time T from disappearance of the current optotypes.

The test optotypes in the red-green chart, the radial line chart for astigmatism test, and the binocular vision test chart exemplified in FIGS. 3D to 3G are larger in size and very different in shape. Thus, the switching of those test optotypes (charts) is easily visually perceivable. The switching of those test optotypes also may be controlled so that next optotypes (charts) appear after the time T from disappearance of the current optotypes (charts) in the same manner as the visual acuity test optotypes (charts). However, when such test optotypes (charts) disappear for switching to another, some persons may feel it lengthier. In the present embodiment, accordingly, as to the optotypes obviously visually perceivable when switched to another, the screen image of the display 3 is controlled to switch such optotypes quickly (in a shorter time than the time T). Whether or not the optotypes obviously visually perceivable when switched to another should be switched with the disappearance time T can be selected with the selecting unit 22.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. An optotype presenting apparatus for testing a visual function of an eye of an examinee, the apparatus comprising:
    display means including a memory in which a plurality of optotypes are stored and a display on which at least one of the stored optotypes is displayed;
    the display means being placed at a distance for far vision test from the examinee's eye;
    operation means from which an optotype switching signal is output; and
    display control means being capable of switching the optotype on the display so immediately that the examinee cannot identify the switching of the optotype if the examinee can barely read the optotype,
    wherein the display control means controls the display to cause the optotype to disappear once for a duration of time needed for the examinee to readily identify the switching of the optotype without immediately switching the optotype in response to the switching signal of one of an optotype for making the examinee indicate an orientation thereof and an optotype for making the examinee read a letter thereof, and the duration of time for disappearing the optotype is 0.05 second to 1.0 second.

2. The optotype presenting apparatus according to claim 1, wherein the duration of time for disappearing the optotype is 0.1 second to 0.5 second.

3. The optotype presenting apparatus according to claim 1, wherein the operation means is a wireless remote controller.

4. The optotype presenting apparatus according to claim 1, wherein the display control means controls the display to cause the optotype to disappear once for the duration of time needed for the examinee to readily identify the switching of the optotype without immediately switching the optotype in response to the switching signal of one of a Landolt ring optotype and a tumbling optotype as the optotype for making the examinee indicate the orientation thereof.

5. The optotype presenting apparatus according to claim 1, wherein the display control means switches the optotype on the display immediately in response to the switching signal of one of a red-green test optotype, an astigmatism test optotype, a binocular heterophoria test optotype, and a binocular aniseiconia test optotype.

6. An optotype presenting apparatus for testing a visual function of an eye of an examinee, the apparatus comprising:
    a display unit including a memory in which a plurality of optotypes are stored and a display on which at least one of the stored optotypes is displayed,
    the display means being placed at a distance for far vision test from the examinee's eye;
    an operation unit from which an optotype switching signal is output; and
    a display control unit being capable of switching the optotype on the display so immediately that the examinee cannot identify the switching of the optotype if the examinee can barely read the optotype, wherein the display control means controls the display to cause the optotype to disappear once for a duration of time needed for the examinee to readily identify the switching of the optotype without immediately switching the optotype in response to the switching signal of one of an optotype for making the examinee indicate an orientation thereof and an optotype for making the examinee read a letter thereof, and the duration of time for disappearing the optotype is 0.05 second to 1.0 second.

7. The optotype presenting apparatus according to claim 6, wherein the duration of time for disappearing the optotype is 0.1 second to 0.5 second.

8. The optotype presenting apparatus according to claim 6, wherein the operation unit is a wireless remote controller.

9. The optotype presenting apparatus according to claim 6, wherein the display control unit controls the display to cause the optotype to disappear once for the duration of time needed for the examinee to readily identify the switching of the optotype without immediately switching the optotype in response to the switching signal of one of a Landolt ring optotype and a tumbling optotype as the optotype for making the examinee indicate the orientation thereof.

10. The optotype presenting apparatus according to claim 6, wherein the display control unit switches the optotype on the display immediately in response to the switching signal of one of a red-green test optotype, an astigmatism test optotype, a binocular heterophoria test optotype, and a binocular aniseiconia test optotype.

* * * * *